United States Patent
Davis et al.

[11] Patent Number: 6,143,004
[45] Date of Patent: Nov. 7, 2000

[54] SUTURING DEVICE

[75] Inventors: Richard M. Davis; Rowland W. Kanner, both of Guntersville, Ala.

[73] Assignee: Atrion Medical Products, Inc., Arab, Ala.

[21] Appl. No.: 09/135,641

[22] Filed: Aug. 18, 1998

[51] Int. Cl.[7] .................................................. A61B 17/04
[52] U.S. Cl. ............................................................ 606/144
[58] Field of Search ................................. 606/144, 139, 606/145–147

[56] References Cited

U.S. PATENT DOCUMENTS

| | | |
|---|---|---|
| 5,047,039 | 9/1991 | Avant et al. . |
| 5,222,508 | 6/1993 | Contarini . |
| 5,304,184 | 4/1994 | Hathaway et al. . |
| 5,306,254 | 4/1994 | Nash et al. . |
| 5,320,632 | 6/1994 | Heidmueller . |
| 5,364,408 | 11/1994 | Gordon . |
| 5,368,601 | 11/1994 | Sauer et al. . |
| 5,374,275 | 12/1994 | Bradley et al. . |
| 5,383,477 | 1/1995 | DeMatteis . |
| 5,391,182 | 2/1995 | Chin . |
| 5,403,329 | 4/1995 | Hinchcliffe . |
| 5,417,699 | 5/1995 | Klein et al. . |
| 5,458,609 | 10/1995 | Gordon et al. . |
| 5,462,561 | 10/1995 | Voda . |
| 5,470,338 | 11/1995 | Whitfield et al. . |
| 5,474,568 | 12/1995 | Scott . |
| 5,573,540 | 11/1996 | Yoon . |
| 5,597,378 | 1/1997 | Jervis . |
| 5,613,974 | 3/1997 | Andreas et al. . |
| 5,665,096 | 9/1997 | Yoon ........................................ 606/139 |
| 5,700,273 | 12/1997 | Buelna et al. . |
| 5,860,990 | 1/1999 | Nobles et al. ........................... 606/144 |
| 5,868,762 | 2/1999 | Cragg et al. ............................. 606/144 |

FOREIGN PATENT DOCUMENTS

| | | |
|---|---|---|
| 4210724 | 7/1993 | Germany . |
| 1093329 | 7/1983 | Russian Federation . |
| 0140557 | 8/1985 | United Kingdom . |

OTHER PUBLICATIONS

International Application Published Under the Patent Cooperation Treaty, WO 95/13021, Oct. 19, 1994, Klein et al.
International Application Published Under the Patent Cooperation Treaty, WO 94/05213, Mar. 17, 1994, Gordon et al.

*Primary Examiner*—Michael Buiz
*Assistant Examiner*—(Vikki) Hoa B. Trinh
*Attorney, Agent, or Firm*—Trexler, Bushnell, Giangiorgi & Blackstone, Ltd.

[57] ABSTRACT

A suturing device includes a housing having an axial lumen therethrough, at least one needle having a tip and being attached to the housing and being capable of traversing along a non-linear path from a first position wherein each such needle is substantially within the housing, to a second position wherein each such needle is substantially extended from the housing, and a suture releasably attached to the housing. The suture can be captured by the tip when each such needle is in the second position and pulled from attachment to the housing when each such needle is moved to the first position. Thereafter, the suture can be released from each such needle and a knot can be formed in the suture to close a wound.

38 Claims, 11 Drawing Sheets

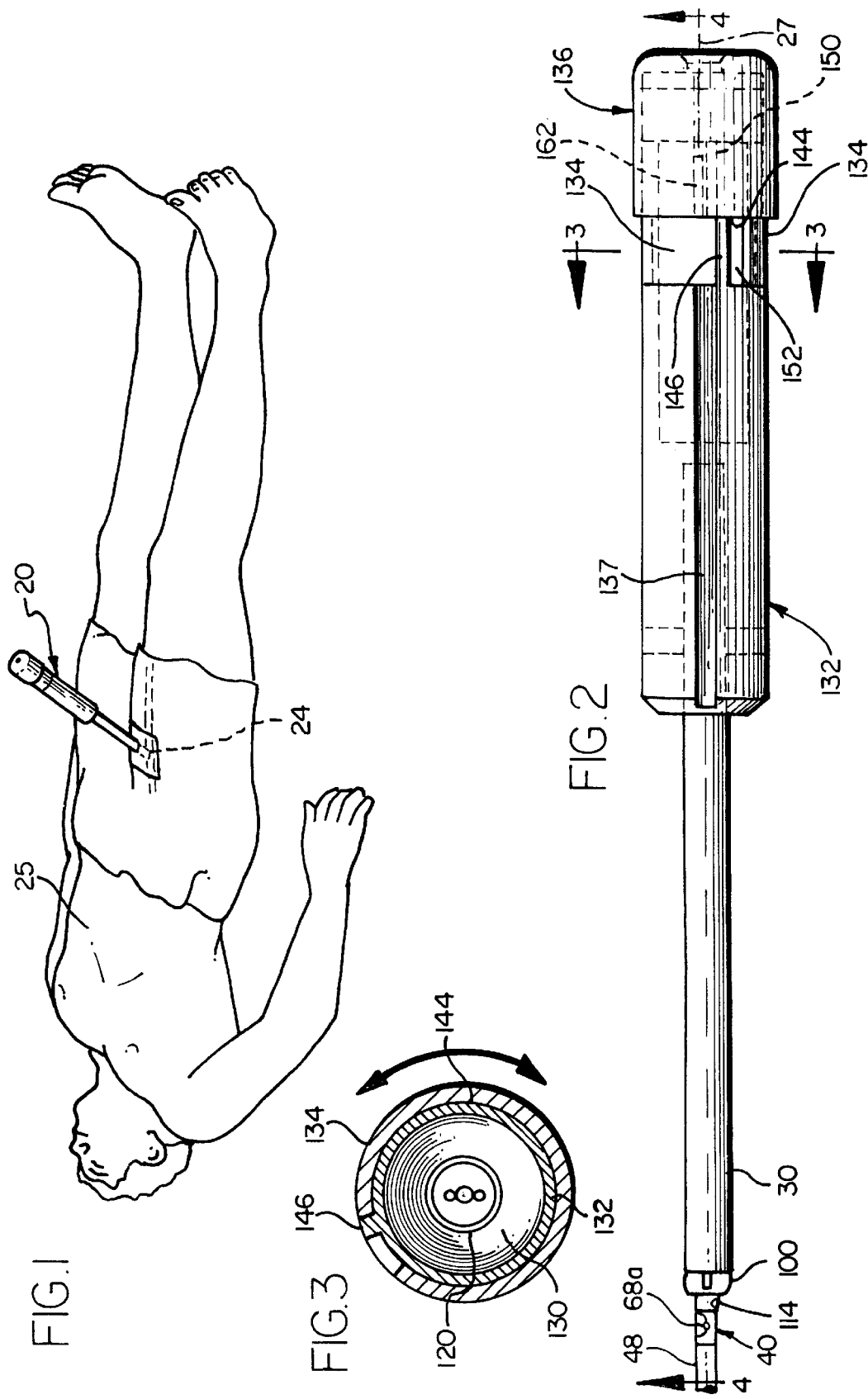

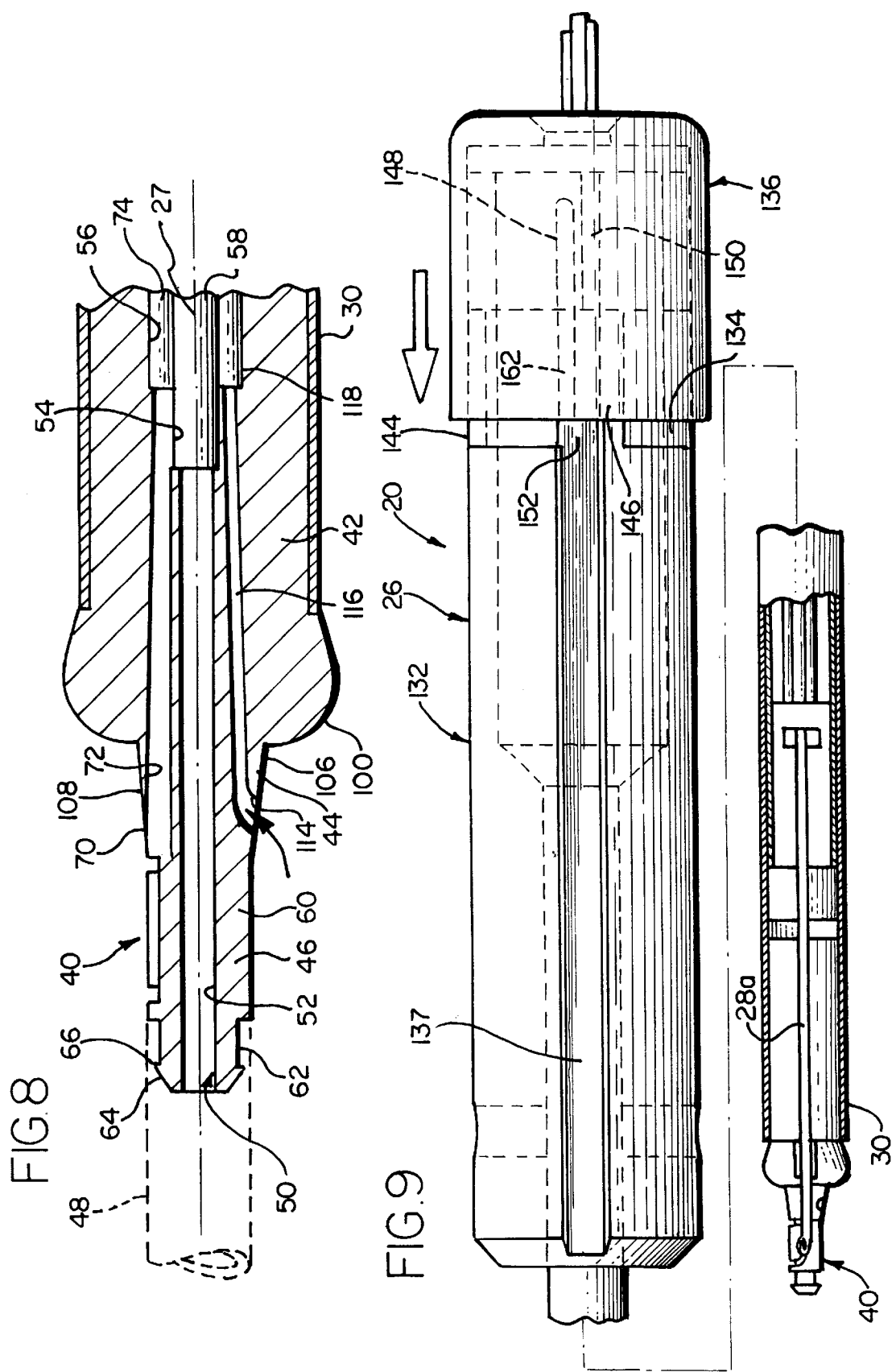

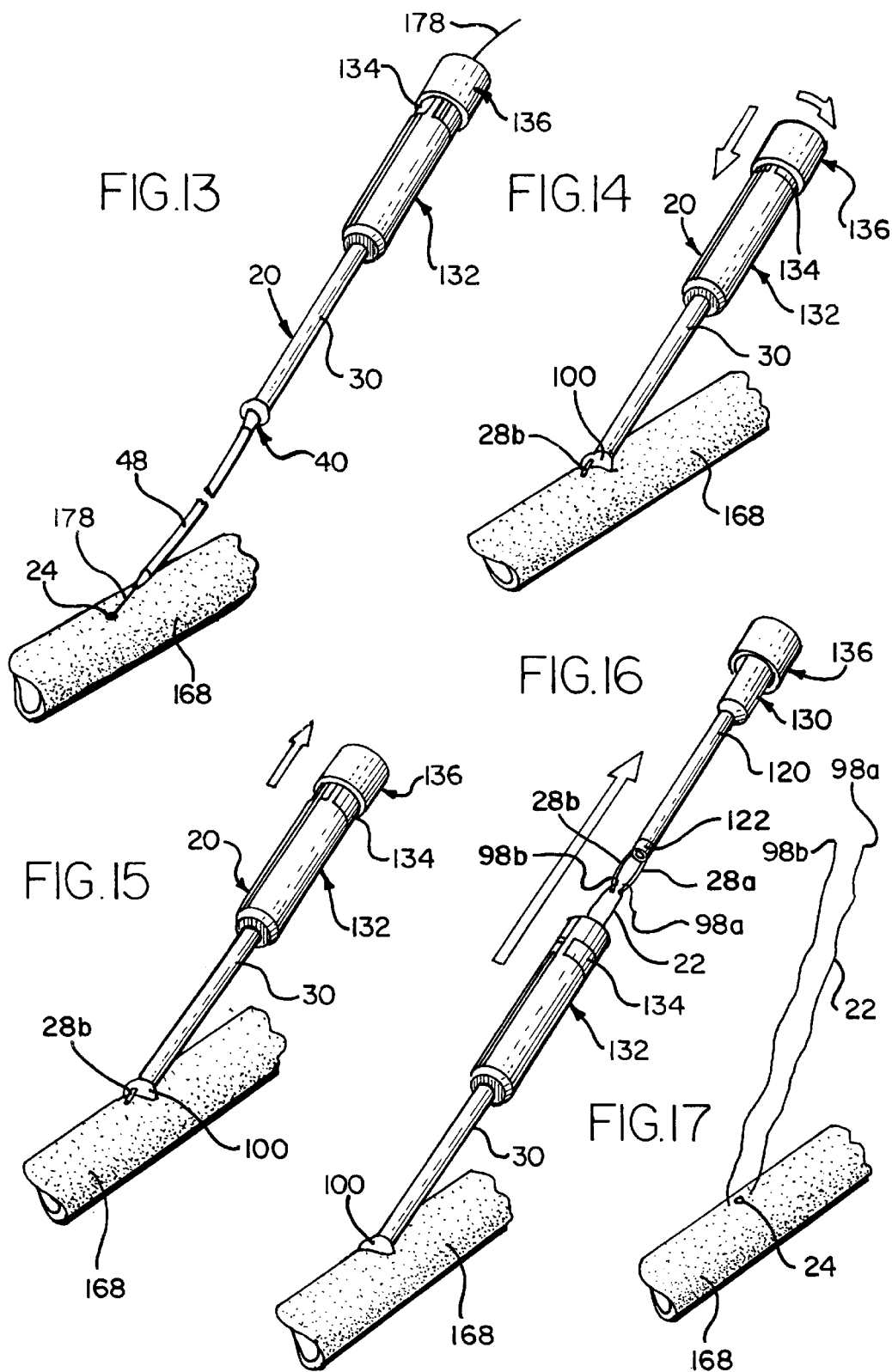

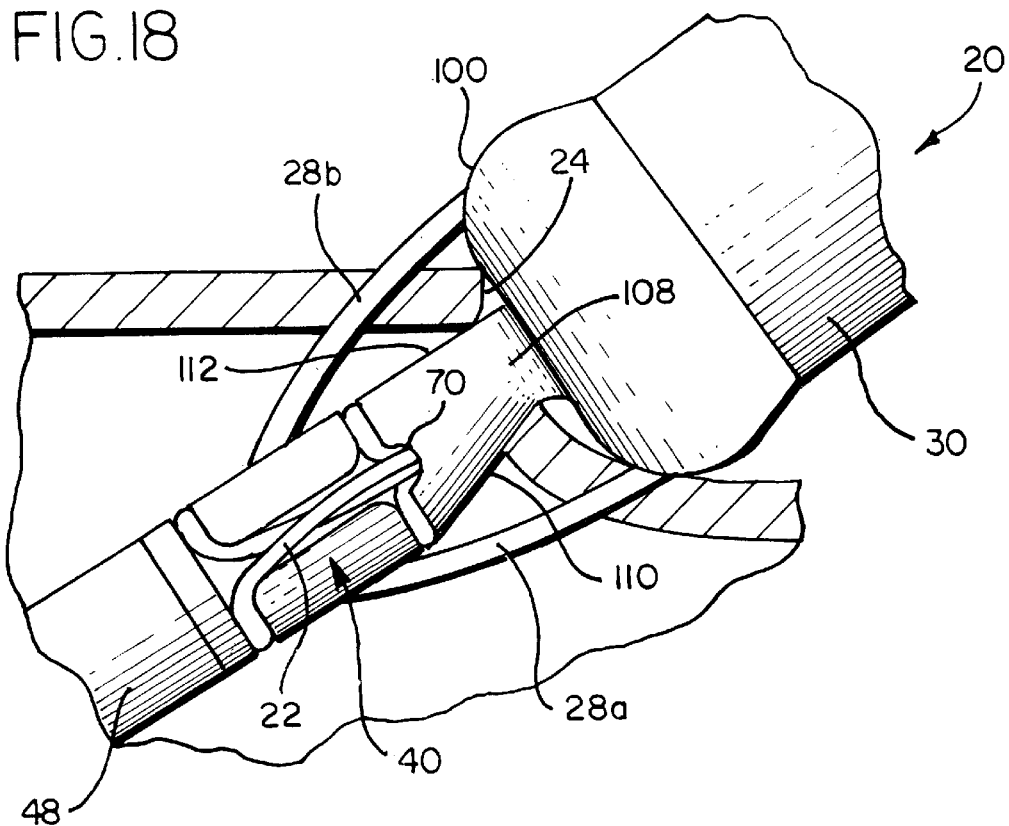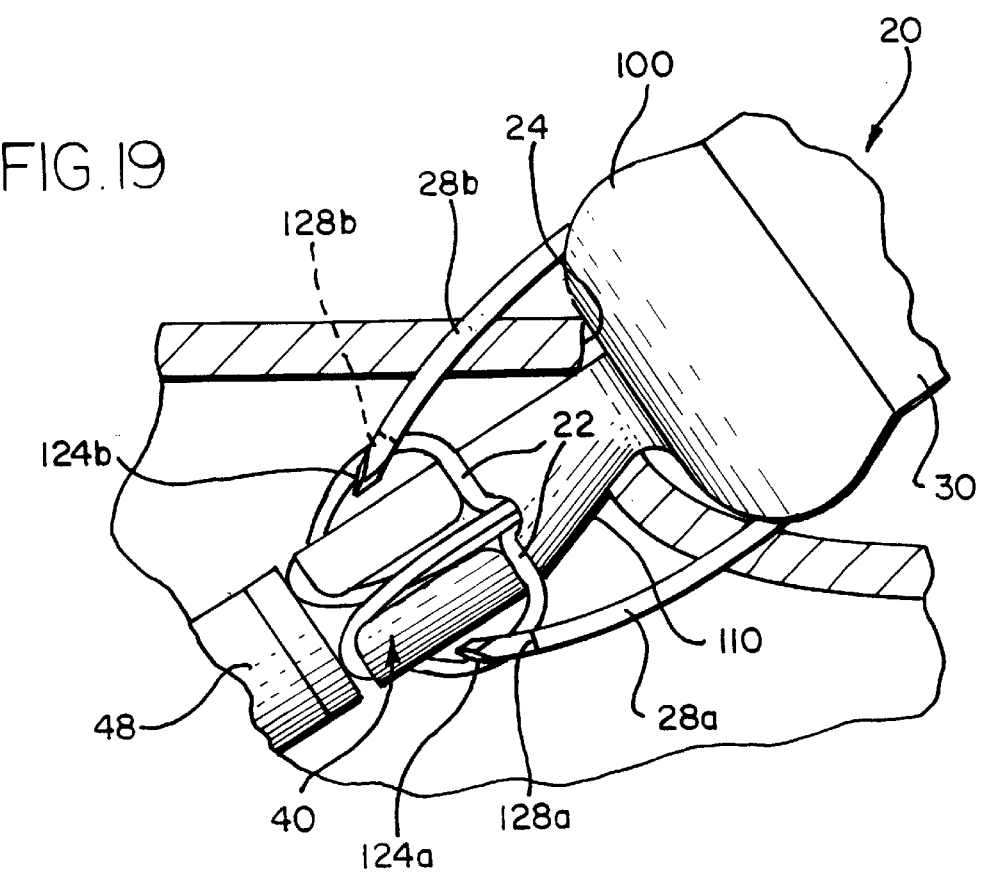

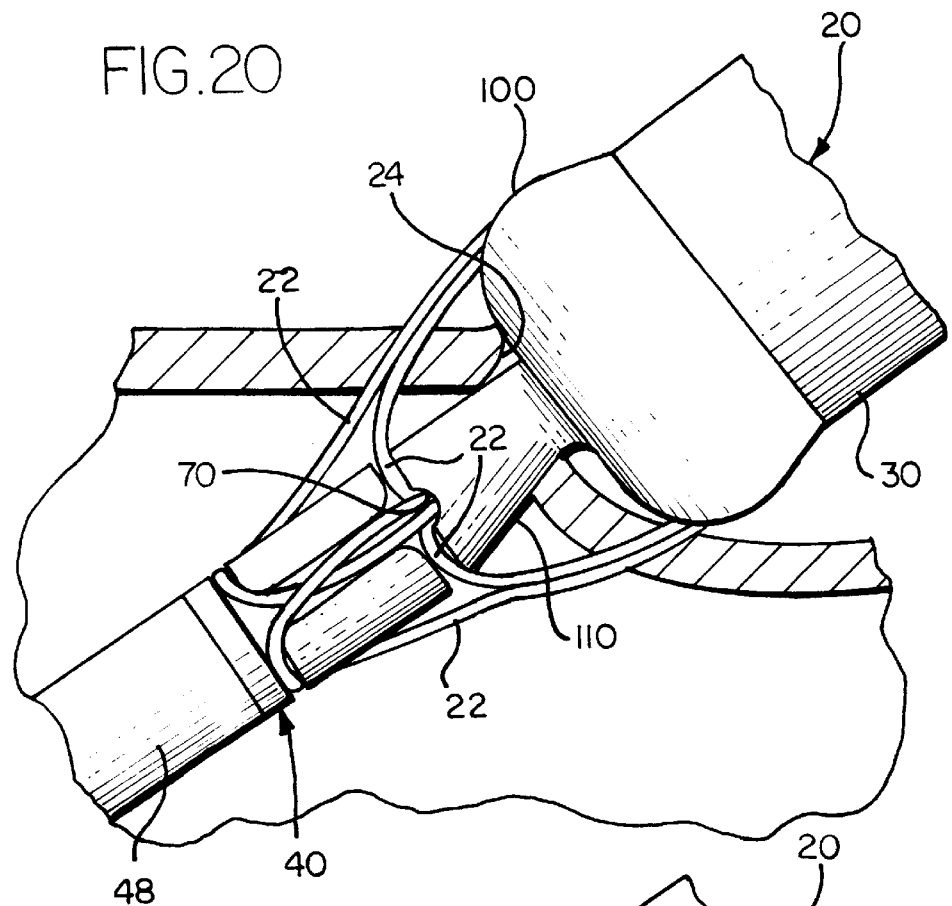
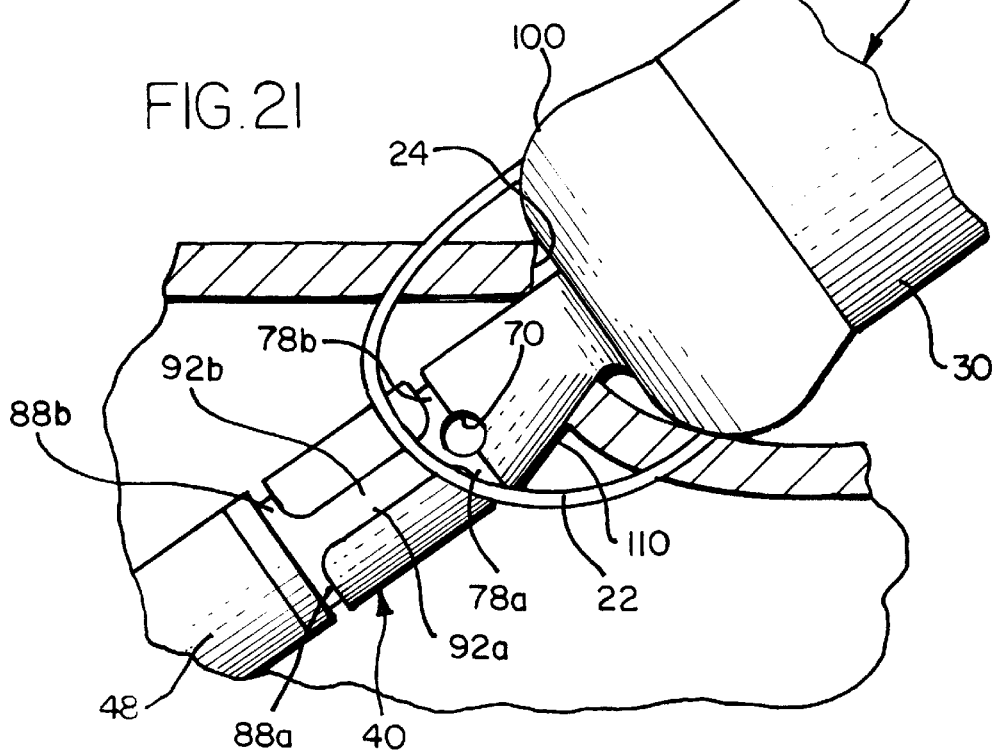

6,143,004

SUTURING DEVICE

BACKGROUND OF THE INVENTION

This invention is generally directed to a novel suturing device for closing a wound and the method of use thereof. More particularly, the invention contemplates a novel suturing device which is used to close a vascular access site for a catheter or the like, typically the femoral artery in the groin area, or a wound through the skin, and the method of using same.

One prior art method of closing a vascular access site or a wound through the skin is effected by directly applying pressure to the wound site for an extended period of time, which results in discomfort for the patient. Often, this is effected by placing compression bandages or sandbags on the wound site.

Another prior art method of closing a vascular access site or a wound through the skin is effected by placing a bio-absorbable plug into the wound site. When the plug is placed in a vascular access site in a vessel, it is possible for the surgeon to place the plug too far into the vessel, thereby partially or fully blocking the blood flow through the vessel.

The novel suturing device of the present invention eliminates the need for applying pressure to the wound site to close same or for placing a bio-absorbable plug in the wound site. Instead, the surgeon places a single stitch, or multiple stitches, in the wound site to close same using the novel suturing device of the present invention. Advantages and features of the present invention will become apparent upon a reading of the attached specification, in combination with a study of the drawings.

OBJECTS AND SUMMARY OF THE INVENTION

A general object of the present invention is to provide a novel suturing device for closing a vascular access site for a catheter, or the like, typically the femoral artery in the groin area, or a wound through the skin, by providing a stitch of suture therethrough, and the method of using same.

An object of the present invention is to provide a novel suturing device in which the suture is not displaced relative to the needles because the needles travel in a non-linear path such that the needle tips puncture the vessel wall and move inward to capture the suture instead of the suture having to be moved outward for capture by the needle tips.

A further object of the present invention is to provide a novel suturing device that is easy and reliable to use.

Briefly, and in accordance with the foregoing, the present invention discloses a suturing device which includes a housing having an axial passageway therethrough, at least one needle having a tip with a hook-shaped or "French eye," and being attached to the housing and being capable of traversing along a nonlinear path from a first position wherein each such needle is substantially within the housing, to a second position wherein each such needle is substantially extended from the housing, and a suture releasably attached to the housing. The suture is captured by each such tip when each such needle is in the second position and pulled from attachment to the housing when the such needle is moved back to the first position. Each needle is formed from a suitable shape memory material, and may be formed from a suitable stainless grade of spring steel, plastic material or a superelastic alloy, such as nickel titanium, which is sold under the trademark name NITINOL® or TINEL®, such that when each needle is in the first position, it is generally straight; when in the second position, each needles is curved.

In order to form a stitch in a vessel or in skin using the suturing device of the present invention, a tip member on the housing is engaged into the vessel or the skin by passing the tip member through, an opening in the wall of the vessel (i.e., an access site), or through the skin. Thereafter, each such needle is moved from the first position to the second position to capture the suture in the needle tip. Each needle passes through the wall of the vessel or the skin as it travels along the non-linear path from the first position to the second position. When in the second position, the suture is grasped by or engaged with the needle tip. Thereafter, each such needle is moved from the second position back to the first position, and the needle again pass through the wall of the vessel or the skin, along with the suture captured by the needle tip. Next, the suturing device is removed from engagement with the vessel or the skin, while the suture remains engaged therewith. Finally, the suture is removed from engagement with the needle and the ends of the suture are tied together in a knot to form a stitch. When each such needle is extended to the second position, the needle can be revolved around a central axis of the housing to capture the suture in the needle tip.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a perspective view of a patient with the suturing device which incorporates the features of the invention being used to close a vascular access site for a catheter or the like through the femoral artery in the groin;

FIG. 2 is a side elevational view of the novel suturing device, showing some components thereof in phantom lines;

FIG. 3 is a cross-sectional view of the suturing device along line 3—3 of FIG. 2;

FIG. 8 is a partial cross-sectional view of the suturing device showing a distal end of the suturing device;

FIGS. 9 and 10 are side elevational views of the suturing device, showing some components thereof in phantom lines;

FIGS. 13–16 are perspective views of the suturing device being used to a suture a wound site in a vessel;

FIG. 17 is a perspective view of a vessel having the suture engaged therethrough prior to knotting by a surgeon;

FIGS. 18–21 are perspective views of the tip member of the suturing device which has the suture mounted thereon showing the needles engaging the vessel wall, capturing the suture and drawing the suture through the vessel wall;

DETAILED DESCRIPTION OF THE ILLUSTRATED EMBODIMENT

Figure 4:
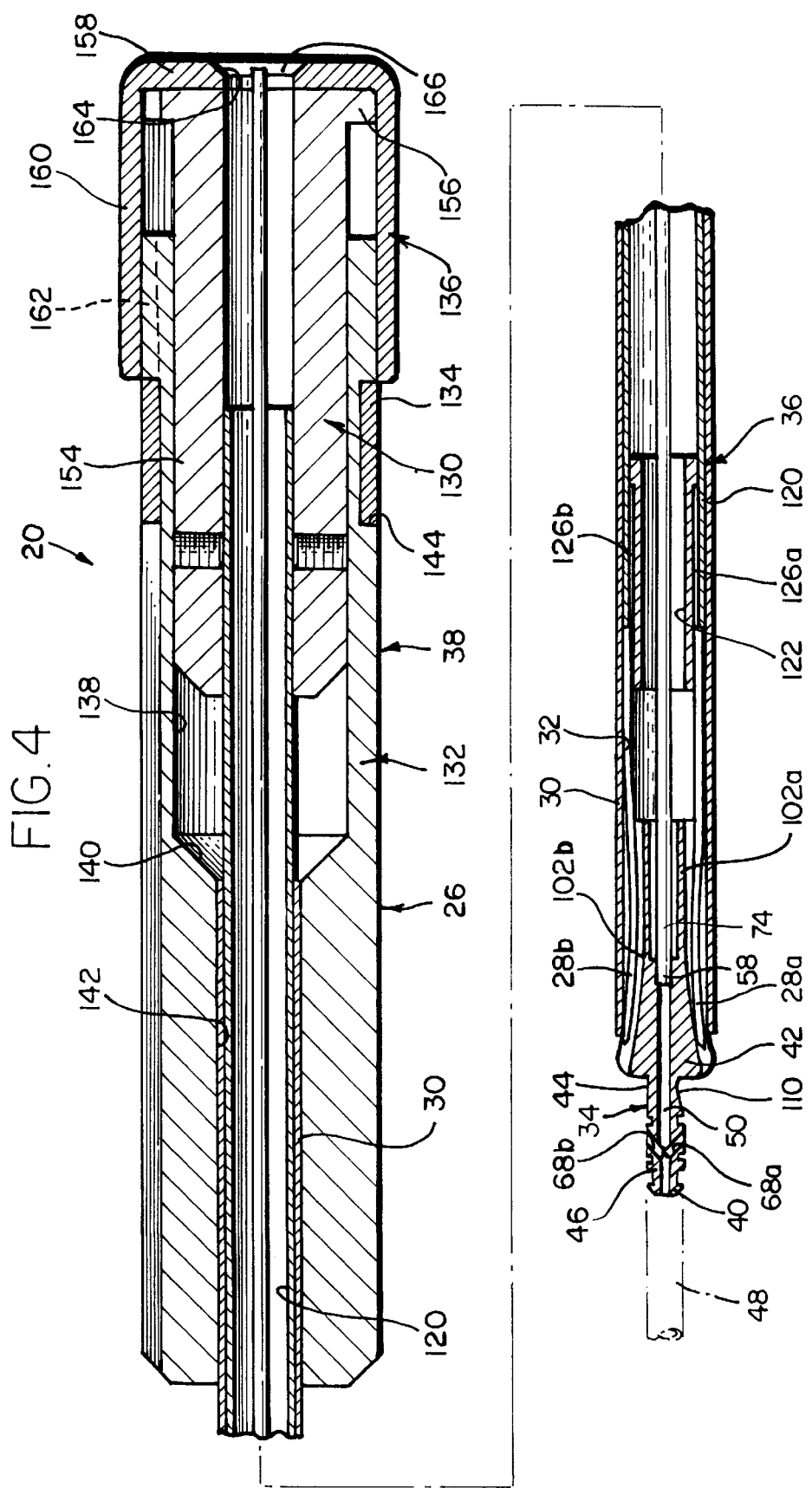
FIG. 4 is a cross-sectional view of the suturing device along line 4—4 of FIG. 2.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to the specific embodiment that is illustrated and described herein.

The present invention provides a novel suturing device 20 which is used to place a suture 22, or multiple sutures, so that closure of a wound 24 in a patient 25 may be accomplished. One application is the closure of a vascular access site, such as in cases of diagnostic or interventional catheterization procedures. Another such application is the closure of a wound through the skin.

The suturing device 20 of the present invention includes a main housing 26 having proximal and distal ends and a central axis 27, and a pair of needles 28a, 28b attached thereto. The term "proximal" when used herein, refers to the portion of the element or component which is closest to the surgeon using the suturing device 20 (and therefore farthest from the patient 25), and the term "distal" when used herein, refers to the portion of the element or component which is farthest from the surgeon using the suturing device 20 (and therefore closest to the patient 25). The housing 26 is formed from a tubular stainless steel barrel 30 having an axial lumen 32 therethrough, a tip assembly 34 connected to the distal end of the barrel 30, a needle carrying and advancing assembly 36 mounted within the axial lumen 32 of the barrel 30, and an actuator assembly 38 attached to the proximal end of the barrel 30.

As best illustrated in FIGS. 4 and 8, the tip assembly 34 is formed from a plastic tip member 40 having a proximal portion 42 which is mounted within the distal end of the barrel 30 and partially protrudes therefrom, and intermediate and distal portions 44, 46 which protrude outwardly from the proximal portion 42, and a flexible sheath 48 which is mounted on a portion of the distal portion 46 of the tip member 40. The distal portion 46 of the tip member 40 has a diameter which is smaller than the proximal portion 42 and is integrally formed with and joined to the intermediate portion 44. The intermediate portion 44 of the tip member 40 is integrally formed with and joined to the proximal portion 42. The sheath 48 may be formed from polyurethane, PVC or polyethylene.

An axial passageway 50 is provided centrally through the tip member 40 for threading a guide wire therethrough. As best illustrated in FIG. 4, the guide wire passageway 50 has a first elongated section 52 which extends from the distal end of the tip member 40 to approximately the middle of the proximal portion 42, a second elongated section 54 axially aligned with the first section 52 which is slightly larger in diameter than the diameter of the first section 52 within the proximal portion 42, and a third elongated section 56 within the proximal portion 42 and axially aligned with the first and second sections 52, 54 and which has a diameter which is slightly larger than the diameter of the second section 54 and extends to the proximal end of the tip member 40. A guide wire tube 58 is attached to the tip member 40 and has a distal end which is seated within the second section 54 of the axial passageway 50 and extends through the third section 56 and the lumen 32 through the barrel 30. The end of the guide wire tube 58 extends out of the proximal end of the housing 26, as described in further detail herein, so that the guide wire can be threaded through the suturing device 20. The guide wire tube 58 does not fill the entire inside of the third section 56.

Figure 5:
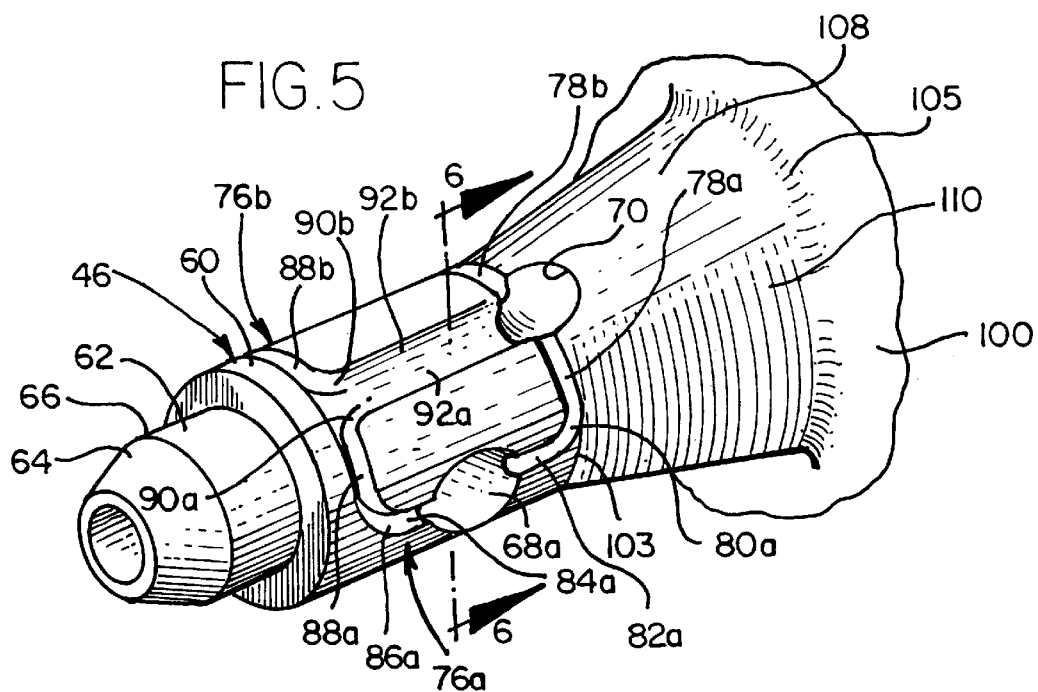
FIG. 5 is a partial perspective view of the suturing device showing a tip portion thereof, wherein grooves are provided for the suture.

As shown in FIGS. 5 and 8, the distal portion 46 of the tip member 40 has a first section 60 which is generally cylindrical, a second cylindrical section 62 which has a diameter that is smaller than the diameter of the first section 60, and a third section 64 connected to the second section 62. Each section 60, 62, 64 is integrally formed with each other. The third section 64 has a surface which extends radially outwardly from the second section 62 to define a shoulder 66, and a distally facing surface which tapers from the outermost point of the shoulder 66 to the distal end of the tip member 40. When the tubular, flexible sheath 48 is attached to the tip member 40, the sheath 48 sits over the second and third sections 62, 64. The shoulder 66 provided by the third section 64 bites into the sheath 48 and prevents the sheath 48 from accidentally disengaging from the tip member 40.

Figure 6:
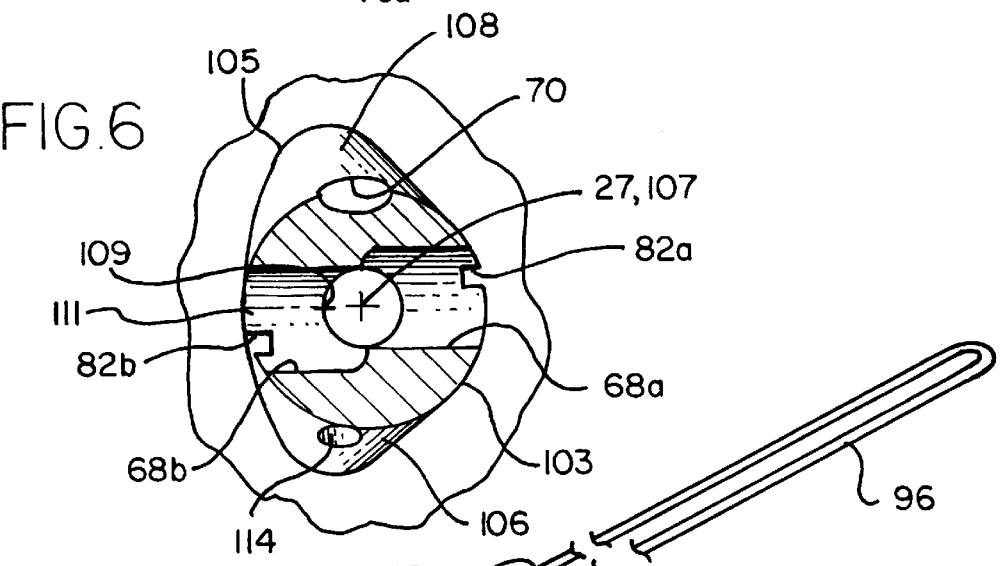
FIG. 6 is a cross-sectional view of the tip portion of the suturing device along line 6—6 of FIG. 5.

The distal portion 46 of the tip member 40, as illustrated in FIGS. 4 and 6, has a pair of passageways 68a, 68b which are generally diametrically opposed from each other. The passageways 68a, 68b are slanted from their respective proximal end to their respective distal end. In addition, the passageways 68a, 68b are in fluid communication with the guide wire passageway 50 through the tip member 40.

As illustrated in FIGS. 5 and 6, an aperture 70 is provided at the juncture point 103 of the distal portion 46 and the intermediate portion 44 and is positioned approximately halfway between the passageways 68a, 68b such that the aperture 70 is proximal of the passageways 68a, 68b. The aperture 70 is in communication with an elongated suture containment passageway 72 extending proximally through the intermediate and proximal portions 44, 42 of the tip member 40. A portion of the suture containment passageway 72 is formed as part of the passageway section 56. A suture containment tube 74 is attached to the suture containment passageway 72 and extends into the lumen 32 of the barrel 30 and has a proximal end which may be sealed. The aperture 70, the suture containment passageway 72 and the suture containment tube 56 are not in fluid communication with the guide wire passageway 50 and the guide wire tube 58.

As best illustrated in FIG. 5, the distal portion 46 of the tip member 40 further has a pair of grooves 76a, 76b in the outer surface thereof. It is to be understood that the grooves 76a, 76b are generally identical, with the exception that they are the mirror image of each other. The grooves 76a, 76b are described with respect to groove 76a. Groove 76a has a first elongated segment 78a which extends outwardly from the aperture 70 along juncture point 103; a first rounded segment 80a which connects the first segment 78a to a second elongated segment 82a; the second segment 82a extends from the first rounded segment 78a to the passageway 68a and is generally perpendicular to the first segment 78a; a third elongated segment 84a which extends from the opposite side of the passageway 68a and is axially aligned with the second segment 82a; a second rounded segment 86a which connects the third segment 84a to a fourth elongated segment 88a; the fourth segment 88a extends from the second rounded segment 86a to a point which is axially aligned with the aperture 70, is generally perpendicular to the third segment 86a and is generally parallel to the first segment 78a; a third rounded segment 90a which connects the fourth segment 88a to a fifth elongated segment 92a; the fifth segment 92a extends from the third rounded segment 90a to the aperture 70, is generally perpendicular to the fourth segment 88a and is generally parallel to the second and third segments 82a, 84a. The fifth segment 92a, 92b of each groove 68a, 68b may be integrally formed with each other as is shown in the drawings or may be separate from each other.

Figure 7:
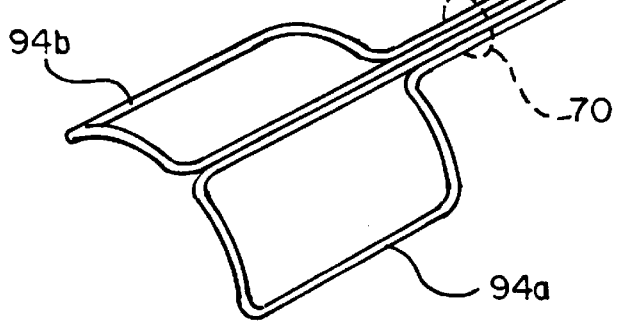
FIG. 7 is a perspective view of a suture as it would be positioned on the suturing device prior to engagement by the needles of the suturing device.
Figure 23:
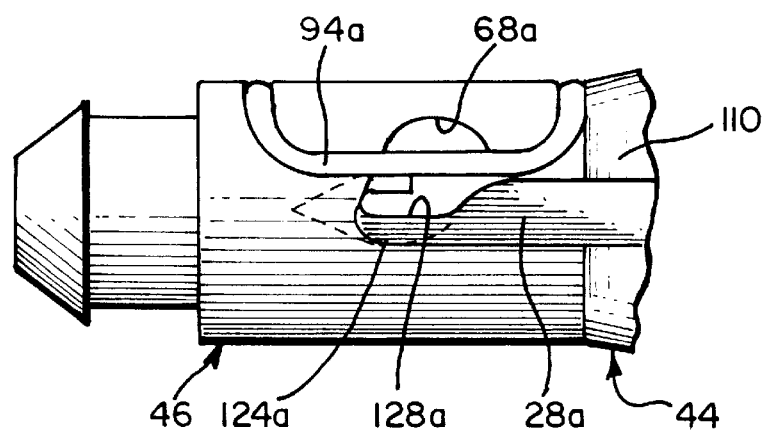
FIGS. 23 and 24 are side elevational views of tip member of the suturing device, with the needles engaged therewith and shown partially in phantom lines for capturing the suture mounted on the tip member.

When the suture 22 is engaged with the suturing device 20, two loops 94a, 94b, see FIG. 7, are formed and are seated within the respective grooves 68a, 68b formed in the tip member 40. Another loop 96 of the suture 22 is placed through the aperture 70 in the tip member 40, extends through the suture containment passageway 72 and into the suture containment tube 74. In addition, the ends or "tails" 98a, 98b of the suture 22 are placed through the aperture 70 in the tip member 40 and extend into the suture containment passageway 72 and may extend into the suture containment tube 74. The suture 22 extends across the passageways 68a, 68b, but does not completely cover the passageways 68a, 68b as shown best in FIGS. 23 and 24.

The proximal portion 42 of the tip member 40 has a rounded ball end 100 at the juncture between the intermediate portion 44 and the proximal portion 42. The ball end 100 has a slightly larger diameter than the diameter of the barrel 30. As best illustrated in FIG. 4, a pair of elongated grooves 102a, 102b are provided along the length of the proximal portion 42 and extend from the proximal end to the distal end thereof. The grooves 102a, 102b are generally diametrically opposed to each other and are aligned with the respective passageways 68a, 68b in the distal portion 46 of the tip member 40. When the proximal portion 42 of the tip member 40 is seated within the distal end of the barrel 30, the grooves 102a, 102b and the inner wall of the barrel 30 define respective needle containment passageways for containing the needles 28a, 28b therein at predetermined times as described herein.

As best illustrated in FIG. 6, the point 103 at which the intermediate portion 44 of the tip member 40 joins with the distal portion 46 is circular in cross-section, the point 105 at which the intermediate portion 44 of the tip member 40 joins with the proximal portion 42 of the tip member 40 is elliptical in cross-section, and the surfaces of the intermediate portion 44 transition from the circular cross-section to the elliptical cross-section. The center point 107 of the circle is aligned with the central axis 27 of the suturing device 20 and the center point 109 of the ellipse is offset therefrom. The ellipse coincides with the circle at point 111 which is aligned with the passageway 68b. Therefore, the intermediate portion 44 has opposite surfaces 106, 108 which taper outwardly from the distal portion 46 to the proximal portion 42 as the intermediate portion 44 transitions proximally from the circle to the ellipse, a surface 110 which tapers inwardly from the distal portion 46 to the proximal portion 42 as the intermediate portion 44 transitions proximally from the circle to the ellipse, and a surface 112 which extends straight from the distal portion 46 to the proximal portion 42 as the intermediate portion 44 transitions proximally from the circle to the ellipse. Tapered surface 108 is proximate to the aperture 70. Tapered surface 110 is proximate to the passageway 68a. Surface 112 is aligned with point 111 and is proximate to the passageway 68b.

As best illustrated in FIGS. 6 and 8, a bleed port 114 for providing a back bleed is provided through the tapered surface 106 of the intermediate portion 44. A bleed passageway 116, see FIG. 8, extends proximally from the bleed port 114 and through the intermediate and proximal portions 44, 42 of the tip member 40. A portion thereof is formed as part of the passageway section 56. A bleed tube 118 is attached to the bleed passageway 116 and extends into the lumen 32 of the barrel 30. The bleed port 114, the bleed passageway 116, and the bleed tube 118 are not in fluid communication with the passageway 50 and the guide wire tube 58. The bleed tube 118 may extend out of the proximal end of the housing 26 as described herein.

The needle carrying and advancing assembly 36 of the housing 26 is formed from a needle tube 120 and a needle carrier 122 which are attached together by suitable means, such as by bonding. The needle tube 120 and needle carrier 122 are mounted within the axial lumen 32 of the tubular barrel 30 and are spaced from the tip member 40 a predetermined distance. As best illustrated in FIG. 4, the needle tube 120 extends outwardly from the proximal end of the barrel 30 a predetermined distance. The needle carrier 122 is tubular and has a portion which is mounted in the axial passageway of the needle tube 120 and a portion which extends outwardly of the distal end of the needle tube 120. The needle tube 120 is formed from a stainless steel alloy and the needle carrier 122 may be formed from ABS or polycarbonate plastic.

Figure 25:
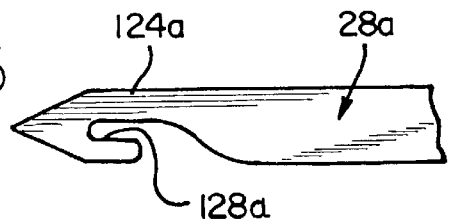
FIG. 25 is an enlarged elevational view of a tip portion of the needle used in the suturing device of the present invention.

The needles 28a, 28b have a distal end having a tip 124a, 124b thereon and a proximal end 126a, 126b. Each tip 124a, 124b has a hook-shaped eye 128a, 128b thereon, such as a "French eye," for capturing the suture 22 therein as described herein. FIG. 25 illustrates a preferred construction of the tip and eye, shown as tip 124a and eye 128a. The eye 128a preferably has a chock therein to prevent slippage of the suture 22 therethrough. The nominal diameter of the suture stock for this needle 28a, 28b having the tip illustrated in FIG. 25 is 0.2 mm and it typically runs between 0.008 and 0.010 outer diameter. The proximal end 126a, 126b of the needles 28a, 28b are attached between the needle tube 120 and the needle carrier 122 by suitable means, such as bonding. The needles 28a, 28b are generally diametrically opposed to each other and are respectively axially aligned with the grooves 102a, 102b and the passageways 68a, 68b in the tip member 40. When in the position shown in FIG. 4 of the drawings (the first position), the needles 28a, 28b extend distally from their attachment to the needle tube 120 and the needle carrier 122, through space between the needle carrier 122 and the tip member 40, and through the respective needle containment passageways defined by the grooves 102a, 102b in the proximal portion 42 of the tip member 40 and the inner wall of the barrel 30. As described herein, the needles 28a, 28b are extended from the needle containment passageways to capture the suture 22 and are moved to a second position.

The needles 28a, 28b are solid and are formed from a suitable shape memory material, and may be formed from a suitable stainless grade of spring steel, plastic material or a superelastic alloy, such as nickel titanium, which is sold under the trademark name NITINOL® or TINEL®. By using the term "shape memory," it means that the needles 28a, 28b are formed into a predetermined shape, curved or non-linear as shown in the drawings, and can be deformed therefrom under a force to straighten, but when the force is removed, the needles 28a, 28b will reassume their naturally curved formation. Prior to engagement with the housing 26, the needles 28a, 28b are formed into a predetermined non-linear or curved formation. Because shape memory alloy is used to form the needles 28a, 28b, the needles 28a, 28b can be generally straightened and can reassume their naturally curved formation. When the needles 28a, 28b are in the first position, the needles 28a, 28b are generally straightened from their normally curved position and are held in this generally straightened formation because of the grooves 102a, 102b and the barrel 30. When the needles 28a, 28b are moved to the second position, the needles 28a, 28b are freed from contact with the grooves 102a, 102b and the barrel 30 and reassume their normally curved position, such that they curve inwardly toward the tip member 40 as more fully described herein. It is to be understood that other suitable elastic materials may also be used so long as it can puncture the vessel wall 168 or the skin, assume a non-linear or curved formation when freed from contact with the grooves 102a, 102b and the barrel 30, and can be deformed to assume a generally straightened formation when retracted into the housing 26.

The actuator assembly 38 of the housing 26 is formed from an actuator 130, a handle 132, a circular ring 134 and a manually grippable member, such as knob 136. The actuator assembly 38 is used to move the needles 28a, 28b distally toward the tip member 40 and proximally away from the tip member 40.

The handle 132 is a generally cylindrical member and may be formed of ABS or polycarbonate plastic. The handle 132 surrounds the proximal end of the barrel 30 and is attached thereto by suitable means, such as bonding or a mechanical attachment, and surrounds the proximal end of the needle tube 120. The handle 132 has an axial passageway therethrough having proximal, intermediate and distal sections 138, 140, 142. The proximal section 138 has a larger diameter than the distal section 142 and the intermediate section 140 tapers from the proximal section 138 to the distal section 142. The barrel 30 is positioned within and attached to the distal section 142 of the handle passageway. The needle tube 120 extends through the intermediate section 140 and into the proximal section 138 of the handle passageway. The actuator 130 is positioned within the proximal section 138 of the handle passageway and extends outwardly therefrom.

At a predetermined spaced position from the proximal end of the handle 132, a groove 144 is provided therein which extends around substantially the entire circumference of the handle 132 with the exception of a stopper portion 146, see FIGS. 2 and 3. The length of the stopper portion 146 is aligned with the central axis 27 of the housing 26. In the portion of the handle 132 between the groove 144 and the proximal end of the handle 132, a slot 148, see FIG. 2, is provided and is axially aligned with the central axis 127 of the housing 26. The slot 148 is spaced circumferentially approximately 15° away from the stopper portion 146 and starts at the groove 144 and ends before the proximal end of the handle 132. In addition, a second slot 150 is provided in the portion of the handle 132 adjacent to the stopper portion 146, spaced from the slot 148, and axially aligned with the central axis 27 of the housing 26. The slot 150 starts at the groove 144 and extends to the proximal end of the handle 132.

To provide a locking function, the ring 134 is seated within the groove 144. The ring 134 may be formed of ABS or polycarbonate plastic and does not extend 360° around the handle 132. Instead, a gap 152, which is larger than the stopper portion 146, is provided along the ring 134 such that the ends of the ring 134 are spaced from each other. The ring 134 can be rotated around the handle 132 by a user to the extent that the gap 152 provides before an end of the ring 134 comes into contact with the stopper portion 146. Detents can be provided to stiffness the rotation of the ring 134 around the handle 132, if desired.

Figure 10:
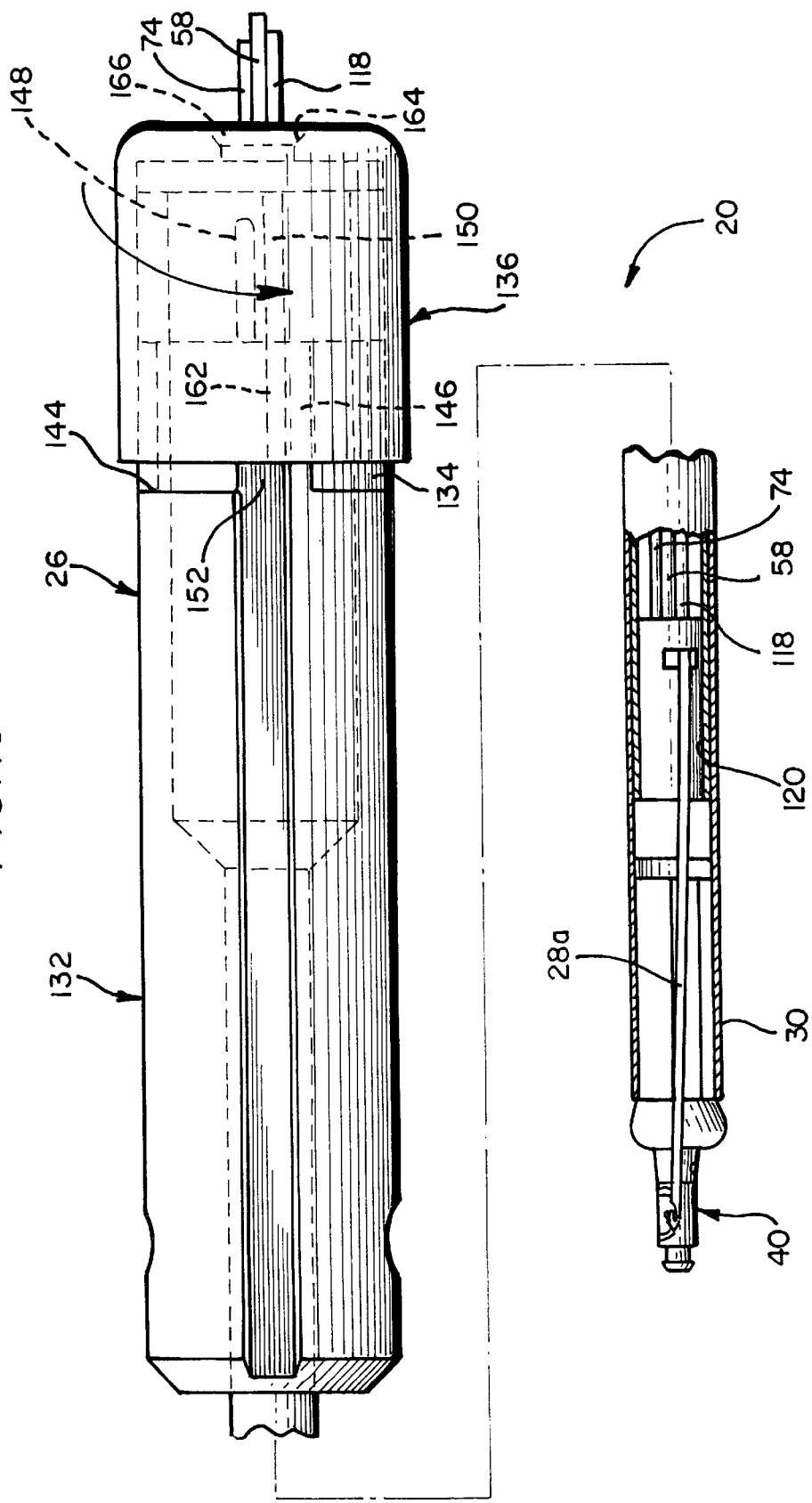

As shown in FIGS. 2, 9 and 10, a suitable indicia, such as flat surface 137, is provided on the handle 132 and extends from the distal end thereof approximately to the groove 144. The flat surface 137 is aligned with the passageway 68a and the tapered surface 110 to allow a user to know where the tapered surface 110 and the passageways 68a, 68b are positioned as described herein. It is to be understood that other indicia than a flat surface 137 may be provided such as a serrated surface or markings provided thereon.

The actuator 130 has a tubular portion 154 which surrounds the end of the needle tube 120 and extends proximally thereof and a skirt 156 which extends radially outwardly from the proximal end of the tubular portion 154. The actuator 130 is seated within the proximal section 138 of the handle passageway and can translate axially relative to the handle 132 along the length of the proximal section 138 of the axial passageway as described herein. The actuator 130 is attached to the needle tube 120 by suitable means, such as by bonding or by mechanical means. The actuator 130 may be formed from ABS or polycarbonate plastic.

The manually grippable member, such as knob 136, is formed from a circular end portion 158 with a circular skirt 160 depending therefrom. A key 162 is provided along the inner surface of the skirt 160 and starts at the distal end thereof. The knob 136 surrounds the proximal end of the handle 132 and the proximal end of the actuator 130 and is attached to the actuator 130 by suitable means, such as by bonding or by mechanical means. The skirt 156 on the actuator 130 abuts against the circular end portion 158 of the actuator 130. The key 162 formed on the inner surface of the skirt 160 is initially seated within the slot 148 provided on the handle 132 but upon proper orientation of the ring 134, the knob 136 can be moved distally, thereby moving the actuator 130 distally, and rotated relative to the handle 132, and thereby rotating the actuator 130, as described herein. An aperture 164 is provided through the end portion 158 of the knob 136 and aligns with the lumen 32 of the barrel 30. The knob 136 may be formed from ABS or polycarbonate plastic. It is to be understood that other types of manually grippable members may be provided for providing the same movements as effected by the knob 136 as described herein.

A sealing means 166 is provided in the aperture 164 in the end portion 158 of the knob 136. As shown in the drawings, the tubes 58, 74 and 118 extend through the sealing means 166 and the sealing means 166 seals around each tube 58, 74 and 118 so as to prevent fluid transfer from within the lumen 32 through the barrel 30 with the exterior of the suturing device 20, and yet the sealing means 166 can be slid along the length of the tubes 58, 74 and 118 without losing its' seal therewith. The sealing means 166 is such that the tubes 58, 74 and 118 can be removed therefrom without losing the fluid tight seal on the end of the barrel lumen 32. If desired, the tubes 74, 118 do not need to extend through the sealing means 166 and can be sealed within the housing 26. If the bleed tube 118 is sealed within the housing 26, a window is provided through the housing 26 so that the surgeon can see the bleed tube 118.

Now that the specifics of the structure of the novel suturing device 20 of the present invention have been described, the method of operation and use of the suturing device 20 to close a wound 24 in a patient 25, such as a wound in a vessel or in the skin, is described. As shown in the drawings, the closing of the wound 24 is described with respect to a vessel 168 under the skin layers 170. In cross-section, the vessel 168 has proximal and distal walls 172, 174.

Figure 12:
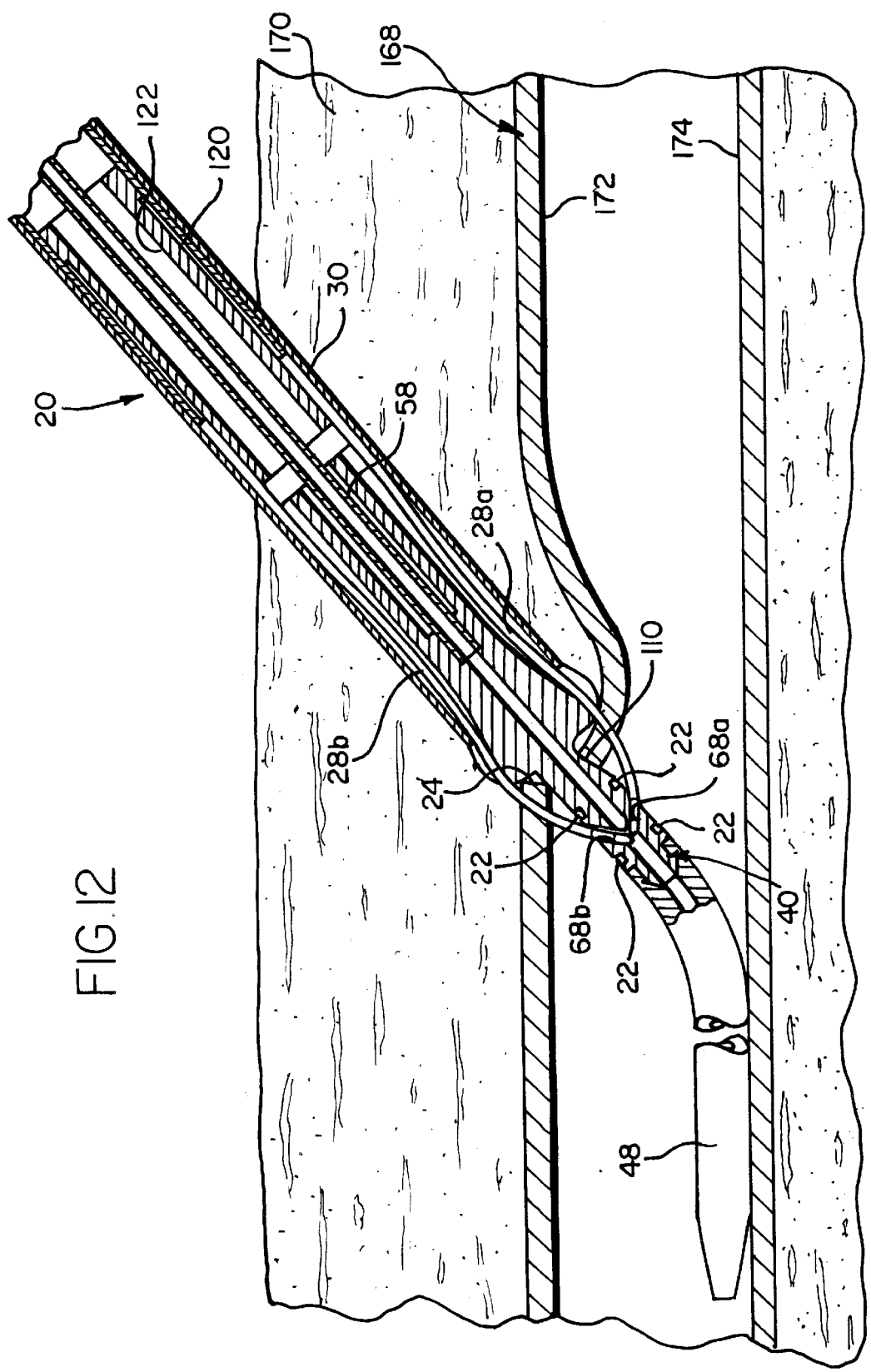

When the suturing device 20 is used to close a vascular access site, there is typically a guide wire 178 in place in the vessel 168, see FIGS. 12 and 13. Initially, as shown in FIG. 2, the suturing device 20 is in a locked position. The key 162, which is attached to the inside of the knob skirt 160, is positioned within the slot 148 and the ring 134 is rotated such that the gap 152 does not align with the key 162, thereby blocking the key 162 from moving the knob 136 distally. The closed end of the slot 148 prevents the user from moving the knob 136 proximally. Rotational motion of the knob 136 is prevented by the sides of the slot 148. The suture 22 is positioned such that the loops 94*a*, 94*b* of the suture 22 are positioned within the respective grooves 76*a*, 76*b* and the loop 96 and the tails 98*a*, 98*b* of the suture 22 are within the suture containment tube 74.

Figure 11:
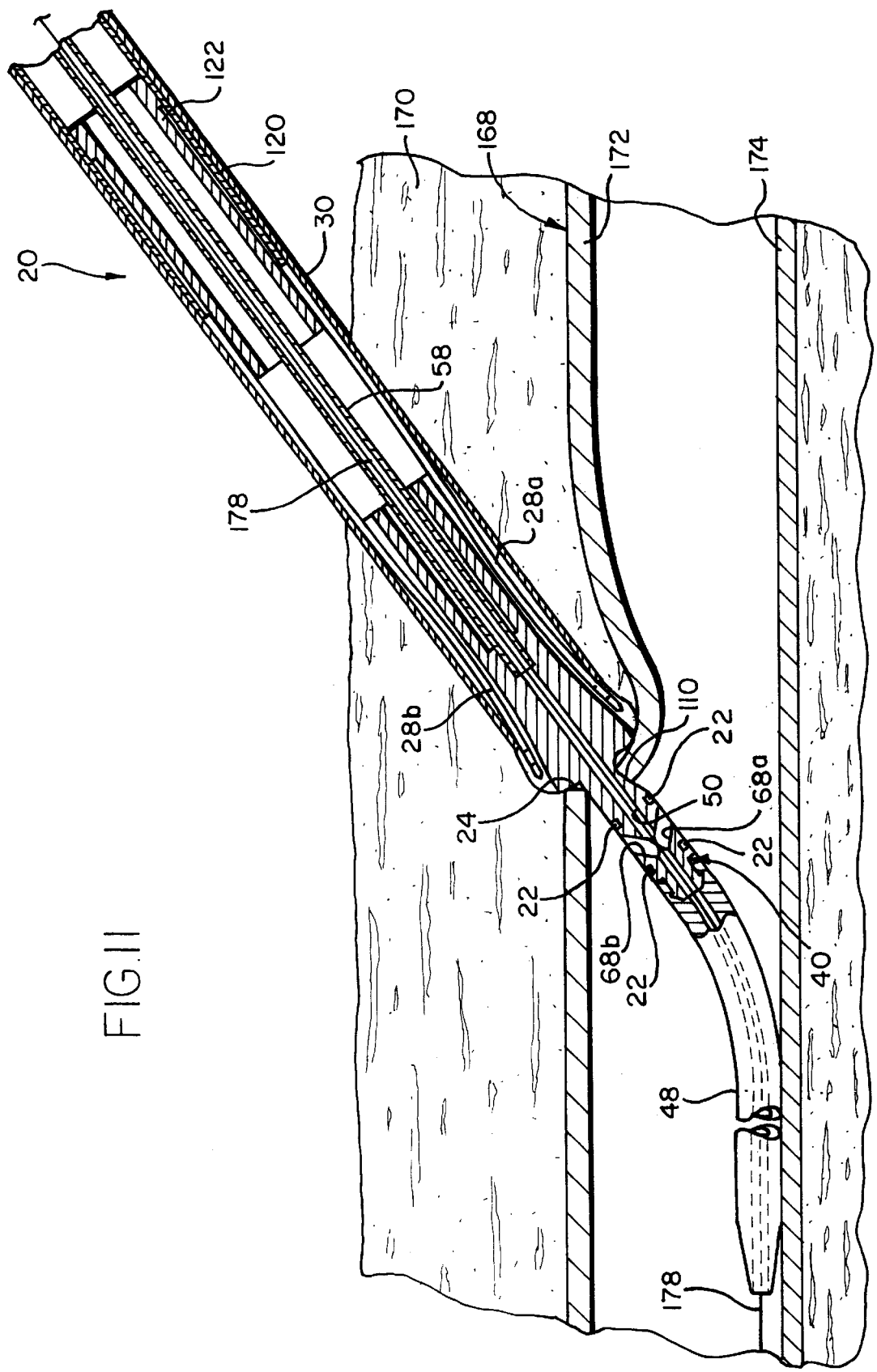
FIGS. 11 and 12 are partial cross-sectional view of the suturing device showing the suturing device engaged with a vessel.

Placement of the suturing device 20 is accomplished by threading the suturing device 20 over the guide wire 178, see FIG. 13, the guide wire 178 passing through the sheath 48, through the passageway 50 in the tip member 40, and through the guide wire tube 58 and exiting out the proximal end of the housing 26, see FIG. 11. The guide wire tube 58 has means on its proximal end for sealing around the guide wire 178. As shown in FIG. 14, the suturing device 20 is advanced distally into the patient 25, through the skin layers 170 and through the access site, until it is determined that the tip member 40 is properly located with respect to the wound 24 to be closed. That is, as shown in FIG. 11, the ball end 100 of the tip member 40 abuts against the vessel proximal wall 168 and the intermediate and distal portions 44, 46 of the tip member 40 are within the vessel 168. The entire suturing device 20 may be rotated to facilitate penetration through the skin layers 170 and the ball end 100 minimizes friction with the tissue. The needles 28*a*, 28*b* are retracted into the needle containment passageways defined by the grooves 102*a*, 102*b* and the inner wall of the barrel 30 and therefore, are not damaged, nor do they interfere with the suturing device 20 if it is rotated to drive the suturing device 20 through the skin layers 170. In this first position, the needles 28*a*, 28*b* are generally straight. Because the back bleed port 114 will be inside the vessel 168 when proper placement is achieved, proper placement is easily verified by the surgeon observing the blood flow in the bleed tube 118. Other means may be used verify proper placement of the suturing device 20, such as fluoroscopy or other means.

When the suturing device 20 is properly inserted into the vessel 168, it is desirable that the needles 28*a*, 28*b* be oriented longitudinally with respect to the vessel 168. Because the surgeon is working in a blind hole, the indicia on the handle 132, such as flat surface 137 as shown in the drawings, provides a means for the surgeon to know the orientation of the needles 28*a*, 28*b* relative to the vessel 168.

The suturing device 20 is inserted into the patient at the same angle relative to the vascular access site or wound site 24 as the angle at which the guide wire 178 is placed, such as a 45° angle, see FIG. 11. Because of the tapered surface 110 on the intermediate portion 44 of the tip member 40, as shown in FIGS. 11 and 12, more of the vessel proximal wall 172 is positioned between the intermediate portion 44 and the outer edge of the ball end 100 of the tip member 40 to obtain a better "bite" of the vessel proximal wall 172.

After is has been determined that the suturing device 20 has been properly placed within the vessel 168, the guide wire 178 is removed by pulling it out of the proximal end of the suturing device 20. The sealing means in the proximal end of the guide wire tube 58 reseals to prevent fluid from escaping from within the guide wire tube 58.

Thereafter, the suturing device 20 is unlocked. The ring 134 is rotated around the handle 132 to align the gap 152 with the key 162 on the inner surface of the knob skirt 160 so as to allow a surgeon to move the knob 136 distally, see FIG. 9. The needles 28*a*, 28*b* are moved distally by pushing the knob 136 distally during which the key 162 moves into the gap 152, thereby causing the attached actuator 130 to travel along the length of the proximal section 138 of the passageway in the handle 132 until the actuator 130 reaches its' limit of travel within the passageway, which, in turn causes the needle tube 120 and the needle carrier 122 to move distally within the barrel 30, see FIGS. 9, 12 and 14. The actuator 130 can be moved distally until the skirt 156 engages against the proximal end of the handle 132. This motion advances the needles 28*a*, 28*b* distally so that the needles 28*a*, 28*b* extend outwardly from the needle containment passageways defined by the grooves 102*a*, 102*b* and the inner wall of the barrel 30 and puncture the vessel proximal wall 172, see FIGS. 12, 14 and 18. As the needles 28*a*, 28*b* are moved distally towards the second position, the needles 28*a*, 28*b*, because of the shape memory alloy, reassume their normally curved position, such that they curve inwardly toward the tip member 40, as the needles 28*a*, 28*b* are released from contact with the grooves 102*a*, 102*b* and the barrel 30. The needles 28*a*, 28*b* curve and move inwardly toward the tip member 40 until the needle tips 124*a*, 124*b* are located within the respective passageways 68*a*, 68*b* in the tip member 40, see FIGS. 12, 18 and 23. The tips 124*a*, 124*b* may enter into the axial passageway 50 through the tip member 40.

Importantly, the needles 28*a*, 28*b* move in a nonlinear movement toward the tip member 40. That is to say, the needles 28*a*, 28*b* move from an outward position to an inward position and the needles 28*a*, 28*b* move toward the suture 22 positioned on the tip member 40. As the needles 28*a*, 28*b* are extended from the needle containment passageways defined by the grooves 102*a*, 102*b* and the inner wall of the barrel 30, the needles 28*a*, 28*b* assume their naturally curved state. Because the needles 28*a*, 28*b* are rigidly and non-removably affixed to the actuator 130, direct one to one longitudinal movement is assured between the components.

The knob 136 is then rotated counterclockwise, see FIGS. 10 and 14, approximately 15° to the limit of its+ rotational motion thereby moving the key 162 counterclockwise to align with the slot 150 and until the key 162 abuts against the stopper portion 146. This rotation is transmitted to the needle carrier 122 via the actuator 130 and the needle tube 120, and causes the proximal ends 126*a*, 126*b* of the needles 28*a*, 28*b* to revolve around the central axis 27 of the housing 26, see FIG. 24. The needle tube 120 and needle carrier 122 rotate within the barrel 30. Because the tips 124*a*, 124*b* of the needles 28*a*, 28*b* are within the passageways 68*a*, 68*b*, the revolving motion of the proximal needle ends 126*a*, 126*b* causes the distal needle tips 124*a*, 124*b* to translate counter to the knob 136 rotational direction by pivoting in the passageways 68*a*, 68*b* in the tip member 40. The revolving movement of the needles 28*a*, 28*b* translates the needles 28*a*, 28*b* into the suture capture position by causing the needles tips 124*a*, 124*b* to translate in direction opposite to the revolving input caused by rotation of the knob 136.

Figure 24:
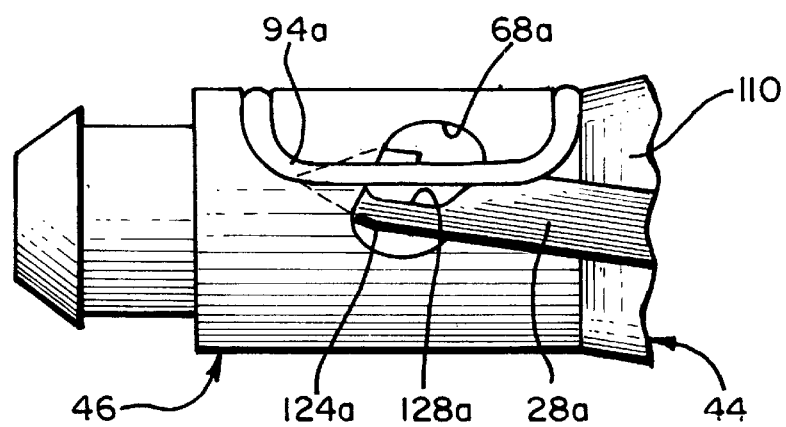

The translation of the needle tips 124*a*, 124*b*, see FIG. 24, places the eyes 128*a*, 128*b* of the respective needle tips 124*a*, 124*b* in position to engage the suture loops 94*a*, 94*b* that lay across the passageways 68a, 68b as the needles 28a, 28b are withdrawn from the tip member 40. It is to be understood that the suture 22 may be arranged so that the needles 28a, 28b displace the suture 22 or are displaced by the suture 22 as the needles 28a, 28b are moved into the passageways 68a, 68b in the tip member 40, thus allowing the eyes 128a, 128b to engage the respective suture loops 94a, 94b as the needles 28a, 28b are withdrawn, without requiring the needles 28a, 28b to translate.

Thereafter, the knob 136 is moved proximally which causes the attached actuator 130 to translate proximally within the handle 132, which, in turn, causes the needle tube 120 and the needle carrier 122 to translate proximally relative to the barrel 30, see FIGS. 15 and 16. The key 162 slides through the slot 150. This movement withdraws the tips 124a, 124b of the needles 28a, 28b from the passageways 68a, 68b and the suture loops 94a, 94b are captured simultaneously by both needles 28a, 28b, see FIG. 19. The movement proximally of the knob 136, actuator 130, needle tube 120 and needle carrier 122 causes the needles 28a, 28b to move proximally through the vessel proximal wall 172, along with the suture 22, now engaged in the needle eyes 128a, 128b, see FIGS. 19 and 20. The eye 128a, 128b geometry is configured to grip the suture 22, approximately 1.5 inches from the end thereof. It is to be understood that the eye 128a, 128b geometry may be such that movement of the suture 22 through the eyes 128a, 128b is allowed. The needles 28a, 28b are moved proximally to retract the needles 28a, 28b into the needle containment passageways defined by the grooves 102a, 102b and the inner wall of the barrel 30 and as the needles 28a, 28b are moved proximally, the needles 28a, 28b reassume the generally straightened formation as they are retracted into the needle containment passageways. The needles 28a, 28b move proximally along a non-linear path away from the tip member 40. That is to say, the needles 28a, 28b move from an inward position to an outward position and the needles 28a, 28b. As the needles 28a, 28b are moved into the needle containment passageways defined by the grooves 102a, 102b and the inner wall of the barrel 30, the needles 28a, 28b generally straighten. Again, because the needles 28a, 28b are rigidly and non-removably affixed to the actuator 130, direct one to one longitudinal movement is assured between the components. As the suture 22 is moved proximally, the loop 96 and tails 98a, 98b are drawn out of the suture containment tube 74, through the passageway 72 and out of the aperture 70, see FIG. 21.

The knob 136, actuator 130, needle tube 120 and needle carrier 122 are continued to be moved proximally so that the key 162 slides along the slot 150 and is released therefrom. Once released, the knob 136, actuator 130, needle tube 120, needle carrier 120 and the needles 28a, 28b with the suture 22 attached thereto are withdrawn from engagement with the barrel 30 and the tip member 40, see FIG. 16. Of course, when the needles 28a, 28b are released from the needle containment passageways, the needles 28a, 28b reassume their naturally curved position, see FIG. 16. The loop 96 and the tails 98a, 98b of the suture 22 are completely drawn out of the suture containment tube 74, through the passageway 72 and out of the aperture 70 such that the suture 22 is free of the tip member 40. As shown in FIG. 16, the suture 22 is drawn through the needle containment passageways defined by the grooves 102a, 102b and the inner wall of the barrel 30 and through the lumen 32 of the barrel 30 as the knob 136, actuator 130, needle tube 120, needle carrier 120 and the needles 28a, 28b are withdrawn proximally from the handle 132, barrel 30 and the tip member 40. When the knob 136, actuator 130, needle tube 120, needle carrier 120 and the needles 28a, 28b are completely withdrawn from the handle 132, barrel 30 and tip member 40, the suture 22 is removed from the needle eyes 128a, 128b and is pulled taut. When in this position, the suture 22 extends through the vessel wall 172 on one side of the wound 24, underneath the wound 24 (i.e., within the vessel 168), and through the vessel wall 172 on the other side of the wound 24. It is to be understood that at this time, only the handle 132, barrel 30, tip member 40, sheath 48, tubes 58, 74 and 118, and suture 22 remain within the patient 25.

Figure 22:
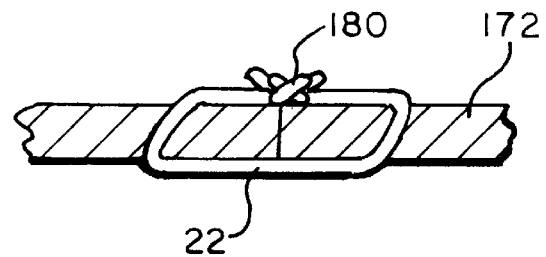
FIG. 22 is a cross-sectional view through the wall of the vessel showing the stitch formed therein.

Thereafter, the barrel 30 and the tip member 40 are withdrawn from the patient 25, leaving the suture 22 in the vessel proximal wall 172. If preferred, the surgeon may re-insert the guide wire 178 before withdrawing the barrel 30 and the tip member 40. Typically, the sheath 48 is left positioned in the wound 24 to reduce bleeding while the suture 22 is knotted. The sheath 48 and the guide wire 178, if re-inserted, are withdrawn completely before the knot 180 is finally tensioned. FIG. 17 shows the suture 22 in its final position where the suture 22 is within the vessel wall 172, ready to be tied. FIG. 22 shows the suture 22 in its final position when the suture 22 is tied into a stitch with a knot 180.

It is to be understood that this same procedure is used for closing any type of wound to be closed using the suturing device 20 of the present invention. For example, a wound in the skin is stitched in the identical fashion, except the surgeon may not be working in a blind hole.

Because the needles 28a, 28b in the present invention travel along a non-linear path, the needle tips 124a, 124b puncture the vessel wall 172 and move inward to capture the suture 22 instead of the suture 22 having to be moved outward for capture. The suture 22 is fixed and is not moved relative to the needles 28a, 28b. The needles 28a, 28b traverse along a non-linear path toward a generally common point within the tip member 40. The non-linear path followed by the needle tips 124a, 124b is controlled by the shape of the needles 28a, 28b and the containment structure for the needles 28a, 28b. In addition, the eyes 128a, 128b on the needle tips 124a, 124b may be located on either the inside, or outside of the needles 28a, 28b.

It is noted that the curved needle 28a, 28b may travel in a path that lies on a geometric plane, or the path may travel on a helical path. It is also to be understood that a similar needle motion could be accomplished via various linkages or cam tracks, and that the needle path may not be an arc, but a different nonlinear form. The needles could also be "split," that is, a flexible needle may be "steered" by selectively advancing one of the two sections of the needle shaft. Additionally, the needle tips could pivot by using a push/pull element.

It is to be understood that other types of manually grippable members may be provided for providing the same movements as effected by the knob 136. For example, the key 162 on the knob 136 can ride along a cam slot so as to effect the distal movement at the same time that the rotation of the knob 136 occurs.

Because of the type of material that is used for the needles 28a, 28b in the illustrated embodiment, a shape memory material, the needles 28a, 28b can be generally straightened from their naturally curved position when the needles 28a, 28b are withdrawn into the needle containment passageways defined by the grooves 102a, 102b and the inner wall of the barrel 30. This shape memory alloy is elastic enough to generally straighten when retracted into the generally straight needle containment passageways, but the predetermined curved shape will be reassumed when the needles 28a, 28b are extended such that the tips 124a, 124b of the needles 28a, 28b will be is able to enter into the passageways 68a, 68b within the tip member 40. Again, it is envisioned that other types of elastic materials can be used, such as stainless steel or plastic, so long as it can puncture the vessel wall 168 or the skin, assume a non-linear or curved formation when freed from contact with the grooves 102a, 102b and the barrel 30, and can be deformed to assume a generally straightened formation when retracted into the housing 26.

As described herein, the suture 22 is threaded through the aperture 70, through the passageway 72 in the tip member 40 and into the suture containment tube 74. The orientation of the suture loop 96 and the tails 98a, 98b can be varied while still providing the same result. For example, the tails 98a, 98b could be threaded through the aperture 70, through the passageway 72 in the tip member 40 and into the suture containment tube 74 while the loop 96 is completely seated within a groove provided on the tip member 40 such that it does not pass through aperture 70. The important aspect of the orientation of the suture 22 is that a length of the suture 22 overlays each passageway 68a, 68b and that the entire length of suture 22 can be released from engagement with the tip member 40.

It is also to be recognized that the tip member 40, the guide wire tube 58, and the actuator assembly 38 may be of various form, structure, or materials without affecting the function of the suturing device 20.

Moreover, an adhesive can be used to releasably hold is the suture 22 in the grooves 76a, 76b. The tails 98a, 98b can be releasably secured to the suture containment tube 74. A shrink wrap film can be used to cover the tip member 40 while still allowing for passage of the needle tips 124a, 124b therethrough and for allowing release of the suture 22 from the grooves 76a, 76b.

Furthermore, the suturing device 20 of the present invention could be provided with one needle or more than two needles if the application so dictates. The requisite number of passageways are respectively provided.

While a preferred embodiment of the present invention is shown and described, it is envisioned that those skilled in the art may devise various modifications of the present invention without departing from the spirit and scope of the appended claims.

The invention claimed is:

1. A suturing device comprising: a housing comprising a body having opposite ends and a tip member at one end of said body; at least one needle having a tip, said at least one needle being carried by said body, structure for moving said at least one needle in a reciprocating motion from a first position wherein said at least one needle is substantially within said body to a second position wherein said at least one needle is substantially extended from said body and from said second position to said first position, said at least one needle being capable of traversing along a non-linear path from said first position to said second position and from said second position to said first position; and a suture adapted to be releasably attached to said tip member, said suture being capable of being captured by said tip of said at least one needle only when said at least one needle is in said second position and said suture being pulled from attachment to said tip member when said at least one needle is returned to said first position.

2. A suturing device as defined in claim 1, wherein said at least one needle, when in said first position, is generally straight.

3. A suturing device as defined in claim 2, wherein said at least one needle, when in said second position, is curved.

4. A suturing device as defined in claim 3, wherein said at least one needle is formed from a superelastic alloy.

5. A suturing device as defined in claim 4, wherein said superelastic alloy is nickel titanium.

6. A suturing device as defined in claim 1, wherein said at least one needle is formed from an elastic material which are generally straightened when in said first position and which are elastically deformed into a non-linear configuration when in said second position.

7. A suturing device as defined in claim 6, wherein said elastic material is a superelastic alloy.

8. A suturing device as defined in claim 6, wherein said elastic material is stainless steel.

9. A suturing device as defined in claim 6, wherein said elastic material is plastic.

10. A suturing device as defined in claim 1, wherein said housing has a central axis and structure for revolving said at least one needle around said central axis, and said at least one needle being revolved around said central axis to capture said suture in said tip when said at least one needle is in said second position.

11. A suturing device as defined in claim 10, wherein said structure for revolving includes a manually grippable member which is connected to said at least one needle, said at least one needle being revolved around said central axis upon rotation of said manually grippable member.

12. A suturing device as defined in claim 11, wherein said housing further includes a lock which can be engaged to prevent rotation of said manually grippable member and can be disengaged to allow rotation of said manually grippable member.

13. A suturing device as defined in claim 1, wherein said tip member is inserted into a vessel or through the skin.

14. A suturing device as defined in claim 13, wherein said tip member has a first, larger diameter portion which is joined to a second portion which is joined to a third, smaller diameter portion, said second portion having a surface which tapers from said first portion to said third portion.

15. A suturing device as defined in claim 13, further including a ball end portion at the end of said body.

16. A suturing device as defined in claim 13, wherein said tip member has a bleed port therethrough and a bleed tube attached thereto for providing a means for a user to visually indicate when the suturing device is properly inserted into the vessel.

17. A suturing device as defined in claim 13, wherein said tip of said at least one needle extends through a passageway provided in said tip member when in said second position for capturing said suture.

18. A suturing device as defined in claim 17, wherein said suture is mounted in grooves provided in said tip member.

19. A suturing device as defined in claim 17, wherein said tip member has a suture containment aperture therethrough for capturing a portion of said suture within said tip member.

20. A suturing device as defined in claim 19, wherein said tip member has a suture containment tube attached thereto and to said suture containment aperture, said suture containment tube extending into said housing for capturing at least a portion of said suture therein.

21. A suturing device as defined in claim 13, wherein said tip member has an axial passageway therethrough and further comprising a tube having first and second opposite ends, said first end of said tube being attached to said tip member and in association with said axial passageway, said tube extending through said housing, said axial passageway and said tube being capable of accepting an associated guide wire therethrough, and means for sealing said second end of said tube around the guide wire when inserted therethrough.

22. A suturing device as defined in claim 1, wherein said housing includes indicating means for providing an indication of the orientation of said needles in said housing to a user.

23. A suturing device as defined in claim 22, wherein said indicating means comprises a flat surface provided on said housing.

24. A suturing device as defined in claim 1, wherein a pair of needles are provided, each said needle having a tip, and wherein when said needles are in said first position, said tips are spaced apart from each other and wherein when said needles are in said second position, said tips are generally proximate to each other.

25. A method of forming a stitch in a vessel or in skin comprising the steps of:

providing a suturing device comprising a housing including a body having opposite ends and a tip member at one end of said body, at least two needles, each said needle having a tip, said needles being carried by said body, each said needle being capable of traversing along a non-linear path upon moving from a first position wherein said needles are substantially within said body and said tips are spaced apart from each other to a second position wherein said needles are substantially extended from said body and said tips are generally proximate to each other, and a suture having opposite ends, said suture being releasably attached to said tip member, said suture only being captured by said tips when said needles are in said second position and pulled from attachment to said tip member when said needles are returned to said first position;

engaging said housing into the vessel or the skin by passing a portion of said housing through a wall of the vessel or the skin;

moving said needles from said first position to said second position, said needles passing through the wall of the vessel or the skin as said needles travel along said non-linear path from said first position to said second position;

grasping said suture with said tips of said needles when said needles are moved to said second position;

moving said needles from said second position to said first position, said needles again passing through the wall of the vessel or the skin as said needles travel along a non-linear path from said second position to said first position;

removing said housing from engagement with the vessel or the skin; and securing said ends of said suture together.

26. A method as defined in claim 25, wherein in said step of moving said needles from said first position to said second position, when said needles are in said first position, said needles are generally straight.

27. A method as defined in claim 26, wherein in said step of moving said needles from said first position to said second position, when said needles are in said second position, said needles are generally curved.

28. A method as defined in claim 25, further including the step of revolving said needle tips around a central axis of said housing to capture said suture in said tips when said needles are in said second position.

29. A method as defined in claim 25, wherein during said step of removing said housing from engagement with the vessel or the skin, a portion of said housing is removed and said needles are removed while a portion of said housing remains in engagement with the vessel or the skin, and further including the step of pulling said suture generally taut and thereafter removing the remainder of said housing prior to securing said ends of said suture together.

30. A method as defined in claim 25, wherein in said step of engaging said housing into the vessel or the skin, said housing is positioned at an angle of approximately 45° to the vessel or to the skin.

31. A method as defined in claim 25, wherein said housing has a bleed port therethrough and a bleed tube attached thereto and wherein during said step of engaging said housing into the vessel or the skin, blood flows through said bleed tube when blood is contacted by said housing for providing a means for a user to visually indicate when the suturing device is properly inserted into the vessel or the skin.

32. A method as defined in claim 25, further including the step of inserting said housing over a guide wire which has been placed in the vessel or through the skin.

33. A suturing device comprising: a housing comprising a body having opposite ends and a tip member at one end of said body; at least one needle having a tip, said at least one needle being carried by said body, said at least one needle being capable of traversing along a path upon moving from a first position wherein said at least one needle is substantially within said body to a second position wherein said at least one needle is substantially extended from said body, said at least one needle being preformed into a stressed shape such that when in said first position, said at least one needle is straightened and, when said at least one needle is moved from said first position, said at least one needle reassumes a non-linear shape; and said tip member adapted to carry a suture, said suture being capable of being captured by said tip of said needle when said at least one needle is in said second position and said suture being pulled from attachment to said tip member when said at least one needle is returned to said first position.

34. A suturing device as defined in claim 33, wherein said at least one needle is formed from a superelastic alloy.

35. A suturing device as defined in claim 34, wherein said superelastic alloy is nickel titanium.

36. A suturing device as defined in claim 33, wherein said housing has a central axis and structure for revolving said at least one needle around said central axis, and said at least one needle being revolved around said central axis to capture said suture in said tip when said at least one needle is in said second position.

37. A suturing device as defined in claim 33, wherein said tip of said at least one needle extends through a passageway provided in said tip member when in said second position for capturing said suture.

38. A suturing device as defined in claim 33, wherein a pair of needles are provided, each said needle being preformed into a non-linear shape such that when in said first position, each said needle is straightened and, when each said needle is moved from said first position, each said at least one needle reassumes said non-linear shape, and wherein when said needles are in said first position, said tips are spaced apart from each other and wherein when said needles are in said second position, said tips are generally proximate to each other.

* * * * *